United States Patent
Karim et al.

(10) Patent No.: US 8,450,548 B2
(45) Date of Patent: May 28, 2013

(54) PROCESS FOR CONVERTING ALIPHATIC OXYGENATES TO AROMATICS

(75) Inventors: Khalid Karim, Riyadh (SA); Naif Al-Otaibi, Riyadh (SA); Syed Zaheer, Riyadh (SA); Abdulkareem Al-Shabnan, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 141 days.

(21) Appl. No.: 12/733,107

(22) PCT Filed: Aug. 13, 2008

(86) PCT No.: PCT/EP2008/006658
§ 371 (c)(1),
(2), (4) Date: Mar. 23, 2010

(87) PCT Pub. No.: WO2009/021726
PCT Pub. Date: Feb. 19, 2009

(65) Prior Publication Data
US 2010/0185033 A1    Jul. 22, 2010

(30) Foreign Application Priority Data
Aug. 13, 2007  (EP) .................................. 07015872

(51) Int. Cl.
*C07C 1/20*  (2006.01)

(52) U.S. Cl.
USPC ........................................................ 585/469

(58) Field of Classification Search
USPC ........................................................ 585/469
See application file for complete search history.

(56) References Cited

U.S. PATENT DOCUMENTS

| | | | |
|---|---|---|---|
| 3,773,161 A | 11/1973 | Bossi | |
| 3,894,103 A | 7/1975 | Chang et al. | |
| 3,894,107 A | 7/1975 | Butter et al. | |
| 4,025,571 A | 5/1977 | Lago | |
| 4,066,714 A | 1/1978 | Rodewald | |
| 4,156,698 A | 5/1979 | Dwyer et al. | |
| 4,590,321 A | 5/1986 | Chu | |
| 4,724,270 A | 2/1988 | Chang et al. | |
| 4,822,939 A | 4/1989 | Chu | |
| 4,992,611 A | 2/1991 | Morrison | |
| 5,866,741 A | 2/1999 | Wu et al. | |
| 6,126,912 A | 10/2000 | Bourges et al. | |
| 6,372,680 B1 | 4/2002 | Wu et al. | |

FOREIGN PATENT DOCUMENTS

| | | |
|---|---|---|
| DE | 2111398 | 9/1971 |
| WO | 9951549 A1 | 10/1999 |
| WO | WO 03074177 | 9/2003 |
| WO | WO 03089135 | 10/2003 |
| WO | 2005080532 A1 | 9/2005 |

OTHER PUBLICATIONS

Watabase WPI Week 200381; Thomson Scientific, London, GB; AN 2003-877158 XP-0022475735.
"Molecular Sieves"; Kirk Othmer Encyclopedia of Chemical Technology; Fifth Edition, vol. 16; 2006; pp. 811-853.
International Publication No. 03089135 (A); Publication Date: Oct. 30, 2003; Abstract Only; 1 Page.
Extended European Search Report; European Application No. 07015872.0; Date of Mailing: May 14, 2008; 10 Pages.
International Search Report; International Application No. PCT/EP2008/006658; International Filing Date: Aug. 13, 2008; Date of Mailing: Dec. 18, 2008; 4 Pages.
Written Opinion of the International Searching Authority; International Application No. PCT/EP2008/006658; International Filing Date: Aug. 13, 2008; Date of Mailing: Dec. 18, 2008; 6 Pages.

*Primary Examiner* — Thuan D Dang
(74) *Attorney, Agent, or Firm* — Cantor Colburn LLP

(57) ABSTRACT

The invention relates to a process for converting a feed stream comprising oxygenated lower aliphatic hydrocarbon compounds, especially methanol, to a product stream comprising aromatic hydrocarbons, especially BTX, which process comprises a step of contacting said feed with a catalyst composition La-M/zeolite, which consists essentially of from 0.0001 to 20 mass % (based on total catalyst composition) of lanthanum; from 0.0001 to 20 mass % of at least one element M selected from the group consisting of molybdenum, copper, cerium and caesium; zeolite in hydrogen form; and optionally a binder.

20 Claims, No Drawings

PROCESS FOR CONVERTING ALIPHATIC OXYGENATES TO AROMATICS

The invention relates to a process for converting a feed stream comprising oxygenated lower aliphatic hydrocarbon compounds, to a product stream comprising aromatic hydrocarbons, which process comprises a step of contacting said feed with a La-containing zeolite catalyst.

More specifically, the invention relates to a process for converting a feed stream comprising C1-C4 oxygenates to a product stream comprising C6-C8 aromatics.

Such a process is known from patent publication U.S. Pat. No. 4,156,698, wherein a feed comprising C1-C4 monohydric alcohol is converted to a mixture, of aliphatic and aromatic hydrocarbons by contacting said feed with a composite catalyst consisting of a crystalline aluminosilicate zeolite, for example ZSM-5, and an aluminium matrix, modified with a mixture of rare earth metals, including La. A catalyst composition based on zeolite/alumina and containing 0.26 mass % of La is used to convert a methanol feed into gasoline boiling range hydrocarbons. Rare-earth modification of the alumina matrix would reduce decomposition of alcohol into carbon monoxide and hydrogen, and increase conversion to aromatics.

Aromatic hydrocarbon compounds like benzene, toluene and xylenes, together often referred to as BTX, are important building blocks in nowadays petrochemical industries. The general source of these compounds traditionally is refining of petroleum. Given the limitations in fossil petroleum resources, alternative sources for these aromatics are being developed.

Aliphatic oxygenates, which can be obtained from various carbon sources via for example synthesis gas, can be converted into a mixture containing aromatics like BTX; for which reaction various catalysts have already been proposed. For example, in U.S. Pat. No. 3,894,103 aromatisation of a lower oxygenate compound like methanol by contacting with a crystalline aluminosilicate zeolite of specific constraint index and Si/Al ratio is described.

U.S. Pat. No. 4,025,571 discloses a process for making hydrocarbons from C1-C4 monohydric alcohol and/or ethers derived therefrom with a catalyst comprising a crystalline aluminosilicate zeolite of specific constraint index and Si/Al ratio of at least 12. Suitable zeolites are exemplified by e.g. ZSM-5, ZSM-11, ZSM-12, ZSM-35 and ZSM-38 materials in their hydrogen-form.

In U.S. Pat. No. 4,724,270 it is taught that in the conversion of methanol to hydrocarbon the selectivity to aromatics improves if the acidity of the crystalline aluminosilicate zeolite of specific constraint index and Si/Al ratio of at least 12 is reduced by a thermal treatment of said catalyst.

In U.S. Pat. No. 4,822,939 a process for converting a feed stream comprising oxygenated lower aliphatic hydrocarbon compounds to a product stream containing aromatic hydrocarbons is described, comprising a step of contacting the feed with a catalyst composition comprising a aluminosilicate zeolite containing at least 0.2 mass % of gallium, at temperature of 500-650° C., pressure of up to 3.5 MPa and weight hourly space velocity of 1-10.

U.S. Pat. No. 4,822,939 more specifically teaches to use a Ga-containing ZSM-5 type zeolite, having a Si/Al ratio of 5000-35000 before Ga-exchange, to catalytically convert C1-C4 aliphatic oxygenates into C2-C5 olefins with improved yields and reduced formation of C1-C5 paraffin. It is indicated that at least part of the Ga should be present in the zeolite framework in tetrahedral coordination to provide Brönsted acid sites, and the zeolite should be substantially free of aluminium in the framework.

A process for making an aromatics mixture rich in p-xylene from C1-C4 monohydric alcohol and/or ethers derived therefrom with a catalyst comprising a crystalline aluminosilicate zeolite of specific constraint index and Si/Al ratio, and modified with oxides from B, B+Mg, P+B/Mg, or P+B+Mg is disclosed in U.S. Pat. No. 4,049,573.

U.S. Pat. No. 4,066,714 discloses that a catalyst comprising a crystalline aluminosilicate zeolite of crystal size 1-2 micron, of specific constraint index and Si/Al ratio, and modified with small amounts of metal cations of ionic radius >1 Å, specifically Cs or Ba, enhances light olefin production from C1-C4 monohydric alcohol and/or ethers derived therefrom.

DE 2111398 describes a continuous process of making aromatics from methanol and/or di-methyl ether applying a zeolite catalyst, and recycling the product stream after removing aromatics. It is shown that a borosilicate results in higher aromatics yield than a standard ZSM-5 aluminosilicate.

U.S. Pat. No. 4,590,321 reveals that conversion of hydrocarbons to aromatics can be increased if a ZSM-5 type of catalyst is modified with phosphorous oxide by an impregnation/calcination process.

U.S. Pat. No. 6,372,680 B1 and U.S. Pat. No. 6,489,528 B2 disclose a hybrid catalyst system comprising A) a silicoaluminophosphate (SAPO) and B) a solid comprising an aluminosilicate (preferably ZSM-5), a Zn-compound and boron. If A) and B) are applied in two subsequent steps to convert a methanol/water mixture to BTX (especially xylenes) improved BTX selectivity results; although A) and B) alone show very low BTX selectivity starting from methanol.

In WO 03/089135 a mixture comprising liquid hydrocarbons is made from lower aliphatic hydrocarbon oxygenates with a pentasil-type aluminosilicate containing sodium, zinc and a mixture of rare-earth metals including La; this catalyst is indicated to result in high yield of high-octane hydrocarbons with a low aromatics content.

A steamed La-modified ZSM-5/silica/kaolin composition is used as catalyst to make a mixture comprising C2-C4 olefins from methanol in WO 99/51549; showing only 2% methanol conversion.

Because there is a constant need in industry for catalysts and processes with improved performance in terms of overall process economics, it is an object of the present invention to provide a catalytic process for converting a feed stream comprising oxygenated lower aliphatic hydrocarbon compounds to a product stream comprising relatively high amounts of aromatic hydrocarbons, especially BTX.

This object is achieved according to the invention with a process for converting a feed stream comprising oxygenated C1-C10 aliphatic hydrocarbon compounds to a product stream comprising aromatic hydrocarbons, the process comprising a step of contacting said feed with a catalyst composition La-M/zeolite, which consists essentially of from 0.0001 to 20 mass % of La (lanthanum); from 0.0001 to 20 mass % of at least one element M selected from the group consisting of molybdenum (Mo), copper (Cu), cerium (Ce) and caesium (Cs); zeolite in hydrogen form; and optionally a binder (mass % based on total catalyst composition).

The process according to the invention surprisingly shows high productivity in combination with good selectivity in converting a feed stream comprising oxygenated C1-C10 aliphatic hydrocarbon compounds to a product stream comprising aromatic hydrocarbons, esp. BTX. The process is also able to convert aliphatic mixtures, like mixtures of hydrocarbons and oxygenated hydrocarbons to aromatics with a high productivity and with high BTX selectivity.

Within the context of the present invention a zeolite, as comprised in the catalyst composition, is understood to mean an aluminosilicate, an aluminophosphate (AlPO) or a silicoaluminophosphate (SAPO), all being in the so-called hydrogen form. These inorganic porous materials are well known to the skilled man. An overview of their characteristics is for example provided by the chapter on Molecular Sieves in Kirk-Othmer Encyclopedia of Chemical Technology, Volume 16, p 811-853; and also by above-cited patent publications. The zeolite in the catalyst composition used in the process according to the invention is typically a crystalline material with homogeneous pore size and channelling framework structures, and is in its hydrogen or acid form. The zeolite being in the hydrogen form means that its sodium or potassium content is very low, preferably below 0.1, 0.05, 0.02 or 0.01 mass %; more preferably presence of sodium is below detection limits.

The pore size of the zeolite in the catalyst composition used in the process according to the invention is not specifically critical, and can be of small, medium or large size; according to the classification generally used in the art. Preferably, the pores are of medium size, which means the pores are from about 5 to about 7 Å, more preferably 5-6 Å. Most preferably, zeolites with a 10-ring structure are applied in the catalyst composition.

Preferably, the zeolite in the catalyst composition of the invention is an aluminosilicate. Any aluminosilicate that shows activity in converting aliphatic oxygenates to aromatics, before modifying with the specific metals of the invention, may be applied.

Aluminosilicate zeolites can be characterized by the Si/Al ratio of their framework. This ratio may vary widely in the catalyst composition used in the invention. Preferably, the Si/Al ratio is from about 5 to 1000, more preferably from about 8 to 500, or from 10 to 300. Examples of suitable materials include the ZSM-series, beta aluminosilicate, or mixtures thereof. Preferred materials are those known as ZSM-5, ZSM-8, ZSM-11, ZSM-12, ZSM-22, ZSM-23, ZSM-35, ZSM-38, ZSM-48 and ZSM-57; more preferably ZSM-5, ZSM-11, ZSM-23, ZSM-48 and ZSM-57 are used.

Also aluminophosphates can be used as zeolite, like AlPO-5, AlPO-11, ALPO-31 or AlPO-41; preferably those of medium pore size, more preferably of 10-ring structure, like AlPO-11 or ALPO-41 are used.

In another preferred embodiment, the zeolite in the catalyst composition used in the process of the invention is silicoaluminophosphate (SAPO). SAPO materials have properties of both aluminosilicates and aluminophopsphates. Any SAPO that shows activity in converting aliphatic oxygenates to aromatics, before modifying with the specific metals of the invention, may be applied. Suitable materials include those known as SAPO-4, SAPO-5, SAPO-11, SAPO-16, SAPO-17, SAPO-20, SAPO-31, SAPO-34, SAPO-35, SAPO-37, SAPO-40, SAPO-41, SAPO-42 or SAPO-44. Preferred are the medium pore size types, most preferably the 10-ring structure types.

The catalyst composition La-M/zeolite used in the process according to the invention, contains of from 0.0001 to 20 mass % of La, based on total catalyst composition). A certain minimum amount of lanthanum is needed to improve selectivity of the catalyst to form aromatics from aliphatic oxygenates; preferably the catalyst contains therefore at least 0.005, 0.01, 0.05, 0.1, 0.2, 0.5, or even 1 mass % of La. If the zeolite would contain too high an amount of metal, the pores of the zeolite might become at least partly clogged, resulting in a masking effect. The La-content of the catalyst thus preferably at most 15, 10, 8, 6, 5, or even at most 4 mass %.

The catalyst composition used in the process according to the invention, further contains 0.0001-20 mass % of at least one element M selected from the group consisting of molybdenum (Mo), copper (Cu), cerium (Ce), and caesium (Cs).

In a preferred embodiment, the process uses a La—Cs/zeolite catalyst composition. In a further preferred way of operating the process, the catalyst composition contains at least two elements M selected from the group consisting of Mo, Cu, Ce, and Cs. Presence of one or more of these elements is found to increase aromatics production from aliphatic oxygenates. Therefore, the catalyst preferably contains at least 0.005, 0.01, 0.05, 0.1, 0.2, 0.5, or even at least 1 mass % of said elements; but at most 15, 10, 8, 6, or 5 mass %.

Preferably, the process according to the invention applies a catalyst composition La-M/zeolite, consisting essentially of from 0.01 to 20 mass % of La (lanthanum); from 0.01 to 20 mass % of at least two elements M selected from the group consisting of molybdenum (Mo), copper (Cu), cerium (Ce) and caesium (Cs); aluminosilicate or silicoaluminophosphate as zeolite in hydrogen form; and optionally a binder.

In a further preferred embodiment, the process according to the invention applies a catalyst composition La-M/zeolite that contains Zinc (Zn) as a further element in addition to the elements M as defined herein above. Zn may be present in the same amounts as indicated for La and the at least one element M. Such catalysts compositions include La—Mo—Zn/zeolite and La—Mo—Cu—Zn/zeolite.

Preferably, the total metal content of the La-M/zeolite composition used as catalyst in the process according to the invention is from 0.1 to 25 mass %, or from 0.2 to 20 mass %.

The various metal elements contained in the catalyst used in the process of the invention may be present in the zeolite structure as framework or non-framework elements; as counterions in the zeolite; on its surface, e.g. in the form of metal oxides; or be present in a combination of these forms.

The process according to the invention uses a catalyst composition that consists essentially of La-M/zeolite as described above, which can optionally contain a binder, that is a component that does not negatively affect its catalytic performance, but mainly serves to provide physical integrity and mechanical strength to the catalyst particles. A binder may comprise a support or filler, mainly intended to dilute catalyst activity; and also binder material, which serves as a glue to hold the components together; both functions may also be combined in one material. Such binder is known to a skilled person. Examples of suitable materials include aluminas, silicas, clays such as kaolin, or combinations thereof. Preferably the binder, if used, is silica.

The catalyst composition used in the process according to the invention can be prepared by suitable methods of preparing and modifying zeolites, as is well known to the skilled person; including for example impregnation, calcination, steam and/or other thermal treatment steps.

If the catalyst composition in addition to the modified zeolite is to contain a binder, such composition can for example be obtained by mixing the modified zeolite and a binder in a liquid, and forming the mixture into shapes, like pellets or tablets, applying methods known to the skilled person.

In the process according to the invention any hydrocarbon feedstock which comprises oxygenated C1-C10 aliphatic hydrocarbon compounds can be used as feed stream. Oxygenated hydrocarbon compounds are herein defined to include hydrocarbons containing aliphatic moieties and at least one oxygen atom, such as alcohols; ethers; carbonyl compounds like aldehydes, ketones, carboxylic acids.

Preferably, the oxygenated hydrocarbon compounds contain 1 to about 4 carbon atoms. Suitable oxygenated hydrocarbons include straight or branched chain alcohols, and their unsaturated analogues. Examples of such compounds include methanol, ethanol, iso-propanol, n-propanol, dimethyl ether, diethyl ether, methyl ethyl ether, formaldehyde, dimethyl ketone, acetic acid, and their mixtures.

Preferably, the feed stream in the process according to the invention comprises C1-C4 alcohols and/or their derivatives, more preferably the feed comprises methanol and/or its derivatives, like a methanol/dimethyl ether mixture.

The feed stream may further contain one or more diluents, the concentration of which may vary over wide ranges; preferably diluents form about 10-90 vol % of the feed. Examples of suitable diluents include helium, nitrogen, carbon dioxide, and water.

The feed stream may also contain other non-aromatic hydrocarbons, like paraffins and/or olefins; especially C1-C5 hydrocarbons. In a preferred way of performing the process according to the invention, the feed stream contains aliphatic hydrocarbons that are recycled from the product stream, for example after removing aromatic components, and which are then for example mixed with an oxygenates containing stream before contacting with the catalyst composition. The advantage hereof is that a higher conversion to aromatics is obtained, because the catalyst of the invention is also active for converting paraffins and olefins to aromatics.

The invention further relates to a process for converting a feed stream comprising oxygenated C1-C10 aliphatic hydrocarbon compounds and C1-C5 hydrocarbon compounds to a product stream comprising aromatic hydrocarbons, the process comprising a step of contacting said feed with a catalyst composition La-M/zeolite, consisting essentially of from 0.01 to 20 mass % of La (lanthanum); from 0 to 20 mass %, preferably from 0.01 to 10 mass % of at least one element M selected from the group consisting of molybdenum (Mo), copper (Cu), zinc (Zn), cerium (Ce) and caesium (Cs) the total metal content of the composition being 0.2 to 25 mass %; aluminosilicate, aluminophosphate or silicoaluminophosphate as zeolite; and optionally a binder (mass % based on total catalyst composition). Other preferred ways of operating this process are analogous to those discussed above.

The step of contacting the feed stream with the catalyst composition can be performed in any suitable reactor, as known to a skilled man, for example in a fixed bed, a fluidized bed, or any other circulating or moving bed reactor.

The contacting step may be performed at a temperature range of about 250 to 750° C. A higher temperature generally enhances conversion to aromatics, the temperature is therefore preferably at least about 300, 350, or 400° C. Because higher temperatures may induce side-reactions or promote deactivation of the catalyst, the temperature is preferably at most about 700, 600, or 550° C. The reaction temperature preferably ranges between 400 to 550° C.

Suitable pressures to conduct the contacting step are from about atmospheric to 3 MPa, preferably pressure is below about 2.5, 2.0, 1.5, 1.0 or even below 0.5 MPa.

The flow rate at which the feed stream is fed to the reactor may vary widely, but is preferably such that a weight hourly space velocity (WHSV) results of about 0.1-500 $h^{-1}$, more preferably WHSV is about 0.5-250 $h^{-1}$, or 1-100 $h^{-1}$. WHSV is the ratio of the rate at which the feed stream is fed to the reactor (in weight or mass per hour) divided by the weight of catalyst composition in said reactor; and is thus inversely related to contact time.

The product stream in the process according to the invention comprises aromatic hydrocarbons, in addition to saturated and unsaturated aliphatic hydrocarbons, and optionally non-converted oxygenates.

In a preferred way of operating the process according to the invention, yield of aromatics is further increased by feeding the product stream to a subsequent second reaction step, wherein the reaction mixture made is contacted with a further catalyst composition to increase the contents of aromatics, for example by catalytically converting aliphatic hydrocarbons, especially olefins, present in the product stream. Suitable further catalysts include the catalyst composition of the invention, and any aromatization catalyst mentioned in the prior art.

The invention will now be further illustrated with below described experiments.

COMPARATIVE EXPERIMENT A

Aluminosilicate ZSM-5 (from Zeolists) was calcined at 550° C. Catalyst particles of 40-60 mesh size were loaded into a tubular fixed bed reactor for the conversion of methanol. The reaction was conducted at a temperature of 450° C. and pressure of 1 atmosphere at a weight hourly space velocity (WHSV) of 9 $h^{-1}$ with respect to methanol feed. Product stream composition was analysed by standard GC techniques. The results are summarized in Table 1.

Catalyst activity is measured as the amount of liquid organic compounds formed per hour; the amount of liquid organics is taken as direct measure for the amount of aromatic compounds formed. Further in table 1, TMB means trimethylbenzenes; Σ BTX is defined as the mass % of the total BTX in the product divided by the methanol conversion (in mass %) and multiplied by 100; Σ Xylene is mass % of the total xylenes (m,p,o) in the product divided by methanol conversion (in mass %), multiplied by 100.

COMPARATIVE EXPERIMENT B

ZSM-5 (65%) and alumina $Al_2O_3$ (35%) were mixed in water and impregnated with mixture of 1.1% $Re_2O_3$ and dried at 120° C. over night and then calcined at 550° C. Catalyst in 40-60 mesh size was loaded into tubular fixed bed reactor for the conversion of methanol. The reaction was conducted at a temperature of 450° C. and pressure of 1 atmosphere at weight hour space velocity (WHSV) of 9 with respect to methanol feed. The results of test runs are given in table. 1

COMPARATIVE EXPERIMENT C

A catalyst was prepared by ion-exchange and thermal treatment of commercially available aluminosilicate in hydrogen form (H-ZSM-5 from Zeolists), with the desired amount of metals and following known procedures. 0.6 g of lanthanum nitrate (from Fluka) was dissolved in 100 g of distilled water and heated at 60-65° C. with continuous stirring. 10 g of ZSM-5 was added to the lanthanum nitrate solution and heated at 85° C. for 8 hours in a closed vessel (about 2 mass % of La added to ZSM-5); then the material was filtered and washed with 2 liters of hot water. The resultant catalyst slurry was dried in a closed oven at 120° C. for 16 hrs. The dried material was subsequently calcined in a rotary furnace with 1° C. temperature increase per minute to 450° C., and held at that temperature for 6 hrs.

Catalyst of particle size 40-60 mesh was loaded into a tubular fixed bed reactor for the conversion of methanol. The reaction was conducted at a temperature of 450° C. and pressure of 1 atmosphere at a weight hourly space velocity (WHSV) of 9 h$^{-1}$ with respect to methanol feed; results are given in Table 1.

COMPARATIVE EXPERIMENT D

Catalyst was prepared as in Comparative experiment C, but now 5 g of lanthanum nitrate was dissolved in 100 g of distilled water; resulting in about 16 mass % of La added to ZSM-5.

Methanol conversion reaction was performed as in Comparative experiment C; results are given in Table 1.

COMPARATIVE EXPERIMENT E

Analogous to Comparative experiment C a La-modified catalyst was prepared starting from a commercially available beta-zeolite (from Zeolists). Dried and calcined catalyst of 40-60 mesh size and containing about 2 mass % of La was used for conversion of methanol, analogous to Comparative experiment C. Table 1 summarizes the results.

COMPARATIVE EXPERIMENT F

A gallium-containing zeolite catalyst was prepared, following the procedure of U.S. Pat. No. 4,822,939, by first calcining ZSM-5 (from Zeolists) at 538° C. Then 4 g of calcined ZSM-5, 8 g of gallium nitrate in hydrated form, and 60 g of water were put in a teflon bottle, and heated to 150° C. for 18 hours. The resultant product was washed and changed into ammonium form, followed by calcination in air.

Catalyst in 40-60 mesh size was loaded into a tubular fixed bed reactor for the conversion of methanol. The reaction was conducted as in Comparative experiment C, and results are summarized in Table 1.

EXAMPLE 1

Analogous to Comparative experiment C a modified ZSM-5 catalyst was prepared, applying 0.6 g of lanthanum nitrate dissolved in 100 g of distilled water; and 0.5 g of molybdenum oxide, 0.06 g of zinc oxide and 2.6 g of cupric nitrate trihydrated dissolved in 100 g of water at 85° C. Both solutions were mixed and 10 g of ZSM-5 was added to this solution and heated at 85° C. for 8 hours in a closed vessel; resulting in about 2 mass % La, 3 mass % Mo, 0.5 mass % of Zn and 7 mass % of Cu being added to ZSM-5.

Dried and calcined catalyst was used for conversion of methanol, analogous to Comparative experiments C and D. Table 1 shows a marked improvement in productivity and BTX selectivity.

EXAMPLE 2

Catalyst was prepared by ion exchange and thermal treatment of the commercial available ZSM-5 from Zeolists with the desired amount of metals. 0.6 g of lanthanum Nitrate (fluka) was dissolved in 100 g of distilled water and heated at 60-65° C. on with continuous stirring. 0.5 g of molybdenum oxide and 0.06 g of zinc oxide were dissolved into 100 g of water at 85° C. at Ph 5. Both solutions were mixed and 10 g of ZSM-5 was added to this solution and heated at 85° C. for 8 hours in a closed vessel. This represents about La (2%), Mo (3%), Zn (0.5%) added to ZSM-5. Resultant catalyst was filtered and washed with 3 liters of hot water. The resultant catalyst slurry was dried in a closed oven at 120° C. for 16 hrs.

The dried catalyst was calcined in rotary furnace with 1° C. temperature increase per minute till 450° C. and held at 450° C. for 6 hrs.

Catalyst in 40-60 mesh size was loaded into tubular fixed bed reactor for the conversion of methanol. The reaction was conducted at a temperature of 450° C. and pressure of 1 atmosphere at weight hour space velocity (WHSV) of 9 with respect to methanol feed. The results of test runs are given in table 1.

EXAMPLE 3

Analogous to Comparative experiment C a catalyst was prepared by ion exchange and thermal treatment of ZSM-5 (from Zeolists) with 0.6 g of lanthanum nitrate dissolved in 100 g of distilled water, and 0.5 g of molybdenum oxide dissolved in 100 g of water; resulting in about 2 mass % of La and 3 mass % of Mo in ZSM-5. Dried and calcined catalyst of 40-60 mesh size was used for conversion of methanol, analogous to Comparative experiment C. Table 1 summarizes the results.

EXAMPLE 4

Analogous to Comparative experiment C a catalyst was prepared by ion exchange and thermal treatment of ZSM-5 (from Zeolists) with 0.6 g of lanthanum nitrate dissolved in 100 g of distilled water, and 0.7 g of cesium nitrate dissolved in 100 g of water; resulting in about 2 mass % of La and 4.5 mass % of Cs in ZSM-5. Dried and calcined catalyst of 40-60 mesh size was used for conversion of methanol, analogous to Comparative experiment C. Table 1 shows a marked improvement in productivity and BTX selectivity.

COMPARATIVE EXPERIMENT G

Comparative experiment C was repeated, but now a feed consisting of methanol/ethylene/propylene/N2 mixture (36:7.7:6.3:50) is reacted over the catalyst at 450° C. and 1 atm, and with a total flow of 65 cc/min. Results are given in Table 2.

COMPARATIVE EXPERIMENT H

Comparative experiment D was repeated, but now a feed consisting of methanol/ethylene/propylene/N2 mixture (36:7.7:6.3:50) is reacted over the catalyst at 450° C. and 1 atm, and with a total flow of 65 cc/min. Results are given in Table 2.

EXAMPLE 5

Example 2 was repeated, but now a feed consisting of methanol/ethylene/propylene/N2 mixture (36:7.7:6.3:50) is reacted over the catalyst at 450° C. and 1 atm, and with a total flow of 65 cc/min. Results are given in Table 2, and show a significant improvement in productivity and aromatics selectivity over La-modified zeolite and Ga-modified zeolite (CE G and H).

TABLE 1

| Experiment | Methanol Conversion wt % | Productivity (liquid organics) g/hr | increment in productivity relative to Comparative experiment B % | Σ BTX wt % | Σ Xylenes wt % | Σ Aromatics (total) wt % | TMB wt % | increment in Σ BTX relative to Comparative experiment B % | increment in Σ Xylenes relative to Comparative experiment B % | increment in Σ Aromatics relative to Comparative experiment B % |
|---|---|---|---|---|---|---|---|---|---|---|
| Comparative experiment A | 100 | 1 | 33 | 5.95 | 3.19 | 8.69 | 0 | 42 | 25 | 34 |
| Comparative experiment B | 95 | 0.75 | base | 4.2 | 2.55 | 6.50 | 0 | base | base | base |
| Comparative experiment C | 100 | 1.23 | 64 | 8.64 | 4.65 | 11.75 | 1.02 | 45 | 82 | 81 |
| Comparative experiment D | 100 | 0.83 | 10 | 7.13 | 3.68 | 9.85 | 0.27 | 20 | 44 | 52 |
| Comparative experiment E | 100 | 0.43 | −57 | 9.01 | 5.11 | 13.0 | 0.31 | 52 | 100 | 100 |
| Comparative experiment F | 100 | 0.93 | 31 | 7.16 | 3.61 | 8.90 | 0.77 | 20 | 42 | 37 |
| Example 1 | 100 | 1.35 | 80 | 10.15 | 5.52 | 13.4 | 1.83 | 71 | 116 | 106 |
| Example 2 | 100 | 1.86 | 148 | 13.77 | 7.98 | 18.8 | 2.31 | 103 | 212 | 189 |
| Example 3 | 100 | 1.07 | 42 | 7.27 | 4.14 | 9.85 | 1.25 | 22 | 62 | 52 |
| Example 4 | 100 | 1.32 | 76 | 10.63 | 5.52 | 12.88 | 1.03 | 78 | 116 | 98 |

TABLE 2

| Experiment | Methanol Conversion wt % | Productivity (liquid organics) g/hr | increment in productivity relative to Comparative experiment H % | Σ BTX wt % | Σ Xylenes wt % | Σ Aromatics wt % | TMB wt % | increment in Σ BTX relative to Comparative experiment H % | increment in Σ Xylenes relative to Comparative experiment H % | increment in Σ Aromatics relative to Comparative experiment H % |
|---|---|---|---|---|---|---|---|---|---|---|
| Comparative experiment G | 100 | 0.56 | 72 | 16.36 | 8.3 | 21.58 | 1.75 | 71 | 83 | 129 |
| Comparative experiment H | 100 | 0.32 | base | 9.54 | 4.54 | 12.41 | 0.76 | base | base | base |
| Example 5 | 100 | 1.26 | 287 | 38.92 | 17.76 | 48.8 | 2.79 | 307 | 291 | 293 |

The invention claimed is:

1. A process for converting a feed stream comprising oxygenated C1-C10 aliphatic hydrocarbon compounds to a product stream comprising aromatic hydrocarbons, the process comprising:
    contacting said feed with a catalyst composition La-M/zeolite to convert the oxygenated C1-C10 aliphatic hydrocarbon compounds to form the product stream;
    wherein the catalyst composition La-M/zeolite consists essentially of from 0.0001 to 20 mass % (based on total catalyst composition) of lanthanum (La); from 0.0001 to 20 mass % of at least one element M selected from the group consisting of molybdenum (Mo), copper (Cu), cerium (Ce) and caesium (Cs); zeolite in hydrogen form; optionally Zinc (Zn); and optionally a binder and wherein said zeolite is an aluminosilicate or aluminophosphate, and wherein the La-M are present in the zeolite as framework or non-framework elements; and
    converting the oxygenated C1-C10 aliphatic hydrocarbon compounds to form the product stream.

2. The process according to claim 1, wherein the zeolite is of medium pore size, with pores from 5-7 Å.

3. The process according to claim 1, wherein the catalyst composition contains 0.1-10 mass % of La.

4. The process according to claim 1, wherein the catalyst composition contains 0.1 to 10 mass % of at least one element M selected from the group consisting of Mo, Cu, Ce, and Cs.

5. The process of claim 1, wherein temperature is from 250 to 750° C., pressure is from atmospheric to 3 MPa, and WHSV is from 0.1 to 500 h$^{-1}$.

6. The process of claim 1, wherein the catalyst composition La-M/zeolite is La—Mo/zeolite, La—Mo—Cu/zeolite, or La—Cs/zeolite.

7. The process of claim 1, wherein the catalyst composition La-M-Zn/zeolite is La—Mo—Zn/zeolite, La—Mo—Cu—Zn/zeolite, or La—Cu—Zn/zeolite.

8. The process of claim 1, wherein the catalyst composition La-M/zeolite consists essentially of 0.05 to 8 mass % (based on total catalyst composition) of lanthanum (La); and 0.05 to 10 mass % of at least one element M.

9. The process of claim 1, comprising at least two elements M.

10. A process for converting a feed stream comprising oxygenated C1-C10 aliphatic hydrocarbon compounds to a product stream comprising aromatic hydrocarbons, the process comprising:
    contacting said feed with a catalyst composition La—Cs/zeolite to convert the oxygenated C1-C10 aliphatic hydrocarbon compounds to form the product stream;
    wherein the catalyst composition La-M/zeolite, which comprises from 0.0001 to 20 mass % (based on total catalyst composition) of lanthanum (La); from 0.0001 to 20 mass % of caesium (Cs); zeolite in hydrogen form; and optionally a binder; and
    converting the oxygenated C1-C10 aliphatic hydrocarbon compounds to form the product stream.

11. The process according to claim 1, wherein the catalyst composition contains at least two elements M selected from the group consisting of Mo, Cu, Ce, and Cs.

12. The process according to claim 1, wherein the catalyst composition comprises the Zinc (Zn).

13. The process according to claim 1, wherein the feed stream comprises C1-C4 alcohols and/or their derivatives.

14. The process according to claim 13, wherein the feed stream comprises methanol and/or its derivatives.

15. The process of claim 10, wherein the feed stream comprises methanol, ethylene, propylene, and nitrogen.

16. A process for converting a feed stream comprising C1-C5 hydrocarbons and oxygenated C1-C10 aliphatic hydrocarbon compounds to a product stream comprising aromatic hydrocarbons, the process comprising:
contacting said feed with a catalyst composition La-M/zeolite to convert the oxygenated C1-C10 aliphatic hydrocarbon compounds to form the product stream;
wherein the catalyst composition La-M/zeolite, which comprises from 0.0001 to 20 mass % (based on total catalyst composition) of lanthanum (La); from 0.0001 to 20 mass % of at least one element M selected from the group consisting of molybdenum (Mo), copper (Cu), cerium (Ce) and caesium (Cs); zeolite in hydrogen form; and optionally a binder; and
converting the oxygenated C1-C10 aliphatic hydrocarbon compounds to form the product stream.

17. The process according to claim 16, wherein said hydrocarbons are recycled from the product stream.

18. The process of claim 16, wherein the feed stream comprises methanol, ethylene, propylene, and nitrogen.

19. A process for converting a feed stream comprising oxygenated C1-C10 aliphatic hydrocarbon compounds to a product stream comprising aromatic hydrocarbons, the process comprising:
contacting said feed with a catalyst composition La-M/zeolite to convert the oxygenated C1-C10 aliphatic hydrocarbon compounds to form the product stream;
wherein the catalyst composition La-M/zeolite consists essentially of from 0.0001 to 20 mass % (based on total catalyst composition) of lanthanum (La); from 0.0001 to 20 mass % of at least one element M selected from the group consisting of molybdenum (Mo), copper (Cu), cerium (Ce) and caesium (Cs); zeolite in hydrogen form; optionally Zinc (Zn); and optionally a binder; and wherein said zeolite is a silicoaluminophosphate; and
converting the oxygenated C1-C10 aliphatic hydrocarbon compounds to form the product stream.

20. The process of claim 19, wherein the feed stream comprises methanol, ethylene, propylene, and nitrogen.

* * * * *